(12) United States Patent
Davis et al.

(10) Patent No.: US 6,190,350 B1
(45) Date of Patent: Feb. 20, 2001

(54) IMPLANTER DEVICE FOR SUBCUTANEOUS IMPLANTS

(75) Inventors: Craig R. Davis, Newark; John R. Peery, Stanford, both of CA (US)

(73) Assignee: Alza Corporation, Mountain View, CA (US)

(*) Notice: Under 35 U.S.C. 154(b), the term of this patent shall be extended for 0 days.

(21) Appl. No.: 09/217,824

(22) Filed: Dec. 22, 1998

Related U.S. Application Data (60) Provisional application No. 60/068,996, filed on Dec. 29, 1997.

(51) Int. Cl.[7] .................................................. A61M 31/00
(52) U.S. Cl. ............................................................ 604/61
(58) Field of Search ................................ 604/51, 60–64, 604/136, 137, 502, 506, 500, 272, 93.01; 606/116, 117; 600/7

(56) References Cited

U.S. PATENT DOCUMENTS

| | | |
|---|---|---|
| 3,991,750 | 11/1976 | Vickery . |
| 4,096,239 | 6/1978 | Katz et al. . |
| 4,105,030 | 8/1978 | Kercso . |
| 4,111,202 | 9/1978 | Theeuwes . |
| 4,111,203 | 9/1978 | Theeuwes . |
| 4,180,560 | 12/1979 | Katz et al. . |
| 4,203,439 | 5/1980 | Theeuwes . |
| 4,263,910 | 4/1981 | Pardekooper et al. . |
| 4,403,989 | 9/1983 | Christensen et al. . |
| 4,487,602 | 12/1984 | Christensen et al. . |
| 4,659,326 | 4/1987 | Johnson et al. . |
| 4,671,789 | 6/1987 | Laby . |
| 4,784,640 | 11/1988 | Johnson et al. . |
| 4,799,921 | 1/1989 | Johnson et al. . |
| 4,994,028 | * 2/1991 | Leonard et al. ........................ 604/60 |
| 5,035,891 | 7/1991 | Runkel . |
| 5,279,554 | * 1/1994 | Turley ..................................... 604/60 |
| 5,810,769 | * 9/1998 | Schlegel et al. ........................ 604/59 |

* cited by examiner

Primary Examiner—Mark Bockelman
Assistant Examiner—LoAn H. Thanh
(74) Attorney, Agent, or Firm—Steven F. Stone; Pauline A. Clarke; Cindy A. Lynch (57) ABSTRACT

An implanter for inserting subcutaneous implants includes a handle for grasping the implanter during implantation, a hollow cannula receiving the implant, and a rod for releasing the implant from the cannula. The rod is longitudinally fixed within the handle while the cannula slides over the rod to release the implant. The cannula is moved over the rod by a sliding actuator mounted in a track of the handle. The actuator is locked in an extended position to prevent unintended release of the implant. Preferably, the implanter is a single-use device having a actuator locking feature preventing reuse.

12 Claims, 9 Drawing Sheets

IMPLANTER DEVICE FOR SUBCUTANEOUS IMPLANTS

This application claims the benefit under Title 35, United Stated Code, §119(e) of U.S. Provisional Application No. 60/068,996 filed on Dec. 29, 1997.

FIELD OF THE INVENTION

The invention relates to an implanter device and method. More particularly, the invention relates to a hand held implanter for containing and depositing a subcutaneous implant beneath the skin of a patient.

BACKGROUND OF THE INVENTION

Many different types of delivery systems for delivering beneficial agents such as pharmaceuticals for the prevention, treatment, and diagnosis of disease are known in the art. One type of delivery system is the subcutaneous implant which contains a supply of a beneficial agent and is implanted beneath the skin of a patient to deliver the beneficial agent over time. Some of the different types of subcutaneous implants include osmotic drug delivery implants, dissolvable or erodable pellet type implants, and diffusional implants. Some examples of osmotic delivery implant systems are described in U.S. Pat. Nos. 4,111,202; 4,111,203; and 4,203,439.

The process of placing subcutaneous osmotic implants and other types of implants under the skin has previously been performed by use of a trocar system which is a two piece system including a cannula and an obturator. With this system, an incision is first made through the skin and the cannula and obturator are inserted together through the skin. The obturator is then withdrawn leaving the cannula in place as a guide for inserting the implant. The implant is inserted through the cannula while the obturator is used to push the implant to the end of the cannula. The obturator is then used to force the implant out of the cannula while the cannula is withdrawn to deposit the implant in the channel previously occupied by the cannula. The cannula and obturator are then withdrawn completely leaving the implant in place beneath the skin.

This trocar insertion process requires substantial expertise in coordinating the pressing of the obturator and the withdrawing of the cannula to deposit the implant in the channel. If these two processes are not properly coordinated, the implant may be forced into the tissue so that the implant has to make its own channel as it is inserted. Forcing the implant into the tissue causes additional trauma to the tissue and may cause the implant to become damaged by the force exerted by the obturator.

This method of insertion of an implant with a trocar is relatively time consuming and cumbersome. In addition, with this prior art insertion method the removal of the obturator for insertion of the implant through the cannula and the reinsertion of the obturator increase the possibility that sterility of the implant site will be compromised during this process.

An implanting apparatus for use in subcutaneously implanting multiple pellets in animals, disclosed in U.S. Pat. No. 4,105,030, provides a one-handed implanting system which reduces the risk of trauma to the tissue due to forcing the implant into the tissue and reduces contamination. The animal implant apparatus includes a handle, a needle containing the pellets to be implanted, and a rod positioned within the needle for pushing the pellets out of the needle. Once the needle containing the pellets has been inserted subcutaneously, a spring loaded trigger on the handle is activated which causes the needle to be automatically withdrawn by a spring leaving the implanted pellets in place. However, the handle configuration of this implanting device is designed for use in animals, such as cattle, and due to it's size and shape would be difficult to use for inserting implants subcutaneously in humans. Further, it is not possible to control the motion of the needle in this device because the needle will automatically retract upon activation of the trigger. The complex spring loaded propelling system and trigger of this implant apparatus increase the chances that the device will jam and fail to eject the pellets when required.

Accordingly, it would be desirable to provide a device for insertion of subcutaneous implants which would simplify the insertion process, allow one handed implant insertion, provide better control over the insertion process, and improve reliability by avoiding implanter jams.

OBJECTS AND SUMMARY OF THE INVENTION

The implanter according to a preferred embodiment of the present invention addresses the disadvantages of the known implant insertion methods by providing a one piece, hand held implanter which is not susceptible to becoming jammed due to binding of moving parts, and allows better control of the implant insertion process than spring actuated implanters.

According to one aspect of the present invention, an implanter for inserting implants includes a handle for grasping the implanter during insertion of an implant, a rod longitudinally fixed to the handle, and a hollow cannula position coaxially around and longitudinally slidable over the rod. The hollow cannula is movable from an extended position in which an implant is retained in the cannula to a retracted position in which the implant is released from the cannula. An actuator is connected to the cannula and slidable in the track of the handle to move the cannula from the extended position to the retracted position.

According to a further aspect of the present invention, a subcutaneous implant insertion system includes an implanter and a subcutaneous implant contained within a cannula of the implanter. The implanter includes a handle, a rod longitudinally fixed within the handle, a hollow cannula longitudinally slidable on the rod, and an actuator connected to the cannula and longitudinally slidable in the handle to move the cannula from an extended position to a retracted position to release the implant from the cannula.

According to a further aspect of the present invention, a method of inserting a subcutaneous implant with an implanter includes inserting a cannula of an implanter beneath the skin of a patient with an implant positioned within the cannula, manually retracting the cannula to release the implant beneath the skin, and withdrawing the implanter from the patient. The implanter used in the method includes a handle and an actuator attached to the cannula such that by sliding the actuator along a track in the handle, the implant is released.

In accordance with another aspect of the present invention, an implant inserting system includes a vial, an elongated implant secured within the vial, and an implanter. The vial has an opening and a closure for closing the opening. The implant is secured within the vial with a longitudinal axis of the implant aligned with the opening of the vial. The implanter has a handle and an elongated cannula extending from the handle for receiving the implant from the vial. The cannula is configured to be inserted into the vial through the opening to remove the implant from the vial.

According to a further aspect of the present invention, an implant vial includes an implant containing a beneficial agent to be delivered, a vial body having an open end, and an implant holding member positioned within the vial body for retaining a position of the implant within the vial. A tapered mouth positioned in the open end of the vial directs a cannula inserted into the open end of the vial body around the implant. A stopper having a sealing surface is arranged to seal a dispensing opening of the implant to prevent the beneficial agent from leaking from the implant. The stopper also seals the open end of the vial body.

According to another further aspect of the present invention, a kit for inserting an implant and maintaining sterile conditions includes an implanter including a handle, a rod longitudinally fixed within the handle, a hollow cannula longitudinally slidable on the rod, and an actuator connected to the cannula and longitudinally slidable in the handle to move the cannula from an extended position to a retracted position to release the implant from the cannula; a cutting device for making an implanting incision in tissue; supplies for maintaining sterility of the implant insertion process; and wound dressings.

It is an object of the present invention to provide a single device insertion system for inserting subcutaneous implants.

It is another object of the present invention to provide an implanter for one handed operation.

It is a further object of the present invention to provide an implanter for inserting implants which is able to be better controlled than spring actuated implanter devices.

BRIEF DESCRIPTION OF THE DRAWINGS

The invention will be described in greater detail with reference to the accompanying drawings, in which like elements bear like reference numerals, and wherein.

DETAILED DESCRIPTION OF THE PREFERRED EMBODIMENTS

The present invention provides an implanter for subcutaneously inserting implants containing beneficial agents, such as pharmaceuticals for the prevention, treatment, and diagnosis of disease. The implanter 10 according to one embodiment of the present invention is illustrated in the side cross-sectional views of FIGS. 1–3. The implanter 10 includes an ergonomically designed, low profile handle 12, a movable elongated cannula 14, and a rod 16 received within the cannula. The cannula 14 is movable with respect to the rod 16 to release a subcutaneous implant 18 positioned within the cannula. The subcutaneous implant 18 may be either preloaded in the implanter 10 or may be loaded by the user just prior to insertion.

Figure 1:
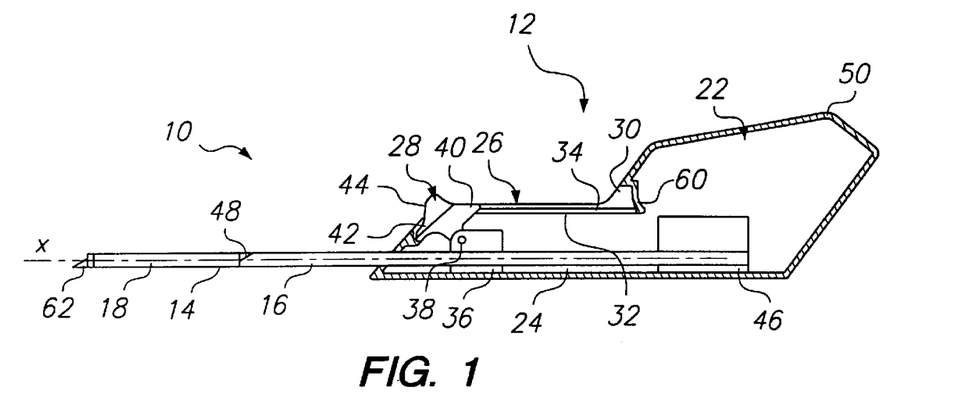
FIG. 1 is a side cross sectional view of an implanter according to the present invention with the cannula extended in a locked position.
Figure 2:
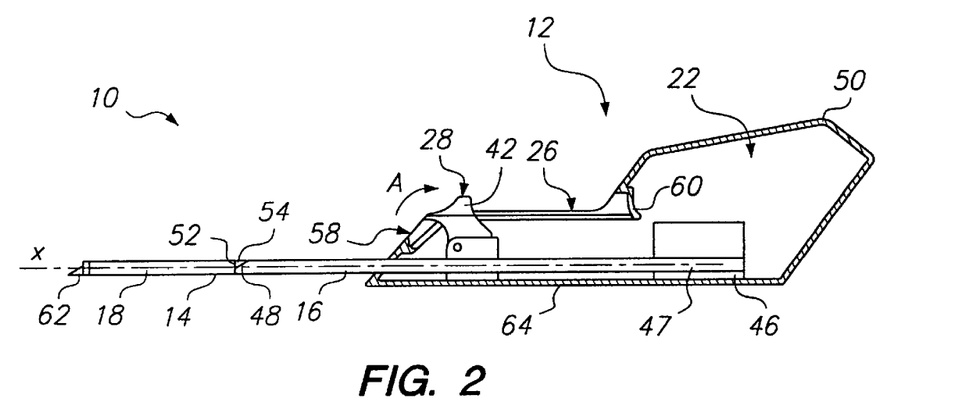
FIG. 2 is a side cross sectional view of the implanter of FIG. 1 with the cannula in an unlocked position prior to retraction of the cannula.
Figure 3:
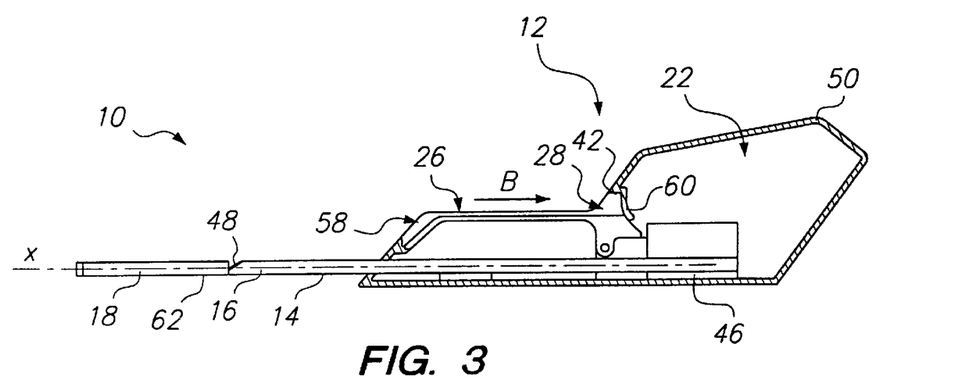
FIG. 3 is a side cross sectional view of the implanter of FIG. 1 with the cannula in a fully retracted position.

The handle 12 includes an enlarged portion 22 and a longitudinally extending portion 24 designed to fit ergonomically into the user's hand. The handle 12 is substantially symmetrical so that the implanter 10 can be used by either right or left handed users. The extending portion 24 of the handle includes a track 26 in which an actuator 28 slides to move the cannula 14. The track 26 is formed by two opposed track side walls 30, one of which is shown in the figures, and a track bottom wall 32. The track 26 also includes a slot 34 extending through a center of the track bottom wall 32 along a length of the track to receive the actuator 28.

The cannula 14 includes a fitting 36 at a proximal end thereof which is secured around the proximal end of the cannula and provides an attachment mechanism for attaching the actuator 28 to the cannula. The fitting 36 may be attached to the cannula in any known manner such as by insert molding, press fitting, adhesive bonding, threading, ultrasonic staking, and the like.

The actuator 28 includes a base 40 which is inserted into the cannula fitting 36 and is pivotally attached to the fitting by a pin 38. The actuator base 40 has a thin profile which extends through the slot 34 in the bottom wall 32 of the track 26 and allows the actuator 28 to slide longitudinally along the track 26. The actuator 28 also includes an enlarged actuator manipulator 42 which is connected to the actuator base 40 for engagement by a user's finger to move the actuator along the track 26. The actuator manipulator 42 may have a ridged, grooved, or knurled slip preventing forward surface 44 which is engaged by the user's index finger.

A longitudinal axis X of the implanter 10 passes through a center of the cannula 14, the rod 16, and through the handle 12. The track 26 extends substantially parallel to the longitudinal axis X. The track 26 has a distal portion 58 which is illustrated most clearly in FIG. 3. The distal portion 58 of the track is formed at an angle of between 25° and 90°, preferably between 45° and 90°, with respect to the longitudinal axis X of the handle. The angled distal portion 58 of the track 26 cooperates with the actuator 28 to provide a locking mechanism which locks the device in the initial loaded position, shown in FIG. 1, and prevents unintended release of the implant 18 from the cannula. The actuator 28 is released from the locked position, illustrated in FIG. 1, by rotating the actuator on the pin 38 in the direction of the arrow A of FIG. 2. When the actuator 28 is in the locked position shown in FIG. 1, a substantial force may be applied longitudinally on the distal end of the cannula 14 without causing the cannula to retract.

Once the actuator 28 has been unlocked, further manual pressure on the actuator manipulator 42 in the direction of the arrow B, shown in FIG. 3, causes the actuator to slide along the track 26 in the direction of the arrow B. As the actuator 28 slides in the direction of the arrow B, the cannula 14 is withdrawn over the rod 16 and the implant 18 is held stationary by the rod causing the implant to be released from the cannula. The actuator 28 allows the user to manually control the motion of the cannula 14 throughout the implant insertion process.

The track 26 also includes a proximal recess 60 which is configured to receive the manipulator 42 of the actuator 28 in the fully retracted position. The proximal recess 60 provides an indication that the cannula 16 has been fully retracted and discourages reuse. Once the manipulator 42 is withdrawn into the recess 60, the actuator 28 and cannula 14 cannot be easily moved back to the initial position. Thus, the recess 60 discourages reuse of the implanter. An additional locking mechanism can also be provided within the handle 12 to more securely hold the actuator 28 in the fully retracted position and prevent reuse. This additional locking mechanism will be described in further detail with respect to the embodiment of FIGS. 4–6.

Although the implanter of FIGS. 1–3 is preferably a single use device, the implanter according to the present invention may also be made for reuse. The reusable embodiment of the implanter will preferably be formed of an autoclavable material for sterilization and reuse.

The rod 16 is positioned with a proximal end 47 fixed within the handle 12 and a distal end 48 extending from the handle. The proximal end 47 of the rod 16 is fixed in place within the handle 12 by a fixing member 46 which is secured to an interior surface of the enlarged portion 22 of the handle 12. The distal end 48 of the rod 16 is configured to engage the implant 18 as the cannula 14 is retracted over the rod. This distal end 48 of the rod, as shown in FIG. 2 has a flat leading edge 52 engaging the implant 18 and a beveled surface 54. The distal end 48 of the rod 16 may also take on other configurations depending on the particular implant to be inserted. Some other distal end configurations include blunt, beveled, concave, and convex end surfaces.

The rod 16 preferably has an outer diameter which is somewhat smaller than an inner diameter of the cannula 14 to provide clearance for a retention element which protrudes slightly from the inner diameter of the cannula to hold the implant 18 in place within the cannula prior to and during implanting. The implant retention element will be described in further detail below with respect to FIGS. 7–10.

The handle 12 of the present invention is designed for one handed operation with the handle grasped between the thumb and the middle finger and a rear surface 50 of the handle resting against the palm of the user while the index finger is used to slide the actuator 28 in the track 26. The handle 12 preferably has a size and shape that can be easily manipulated during implant insertion. Preferably, a length to height ratio of the handle 12 is between 2:1 and 5:1.

The low profile of the handle 12 relative to the cannula 14 allows the user to easily keep the handle parallel to the skin surface to prevent the cannula from diving into other tissue or piercing out through the skin during insertion. The low profile handle 12 includes a bottom surface 64 which is substantially planar and parallel to the cannula 14 so that the handle can remain as close as possible to the skin surface during insertion. In addition, the distance between a bottom of the cannula 14 and the bottom surface 64 of the handle 12 is preferably as small as practically possible.

The implanter 10 allows visual confirmation of the presence of the implant 18 within the cannula 14 by positioning the implant so that a corner of the cylindrical implant extends out of the beveled tip 62 of the cannula. In addition, the distal end 48 of the rod 16 is preferably colored differently than the beveled end 62 of the cannula 14 and the implant 18. The colored distal end 48 of the rod 16 can be seen after the implant has been inserted to confirm that the implant has been left in the patient.

A distal tip 62 of the cannula 14 may be formed at various beveled angles, such as between about 30° and about 45°, or at a sharp point, such as 27° which can cut skin. The preferred design of the cannula tip 62 is a design with a beveled tip which does not cut unbroken skin and does not require special sharps disposal. The cannula 14 of the implanter is preferably inserted into the patient through a small incision made in the patient's skin to minimize scarring.

In operation the implanter 10 is loaded with an implant 18 either manually or with the special loading vial described below with respect to FIGS. 11–13. An incision is made at an implantation site and the cannula 14 is inserted through the incision to a desired depth. Preferably, a depth indicating marker, such as a ring, is provided on the cannula 14 to assist in locating the implant at a particular depth. Once the cannula 14 is placed under the skin at a desired location for the implant the actuator 28 is drawn back manually causing the cannula 14 to be withdrawn over the implant 18 and the rod 16. When the cannula 14 has been fully withdrawn the implanter is withdrawn from the patient leaving the implant 18 in place.

Figures 4, 5:
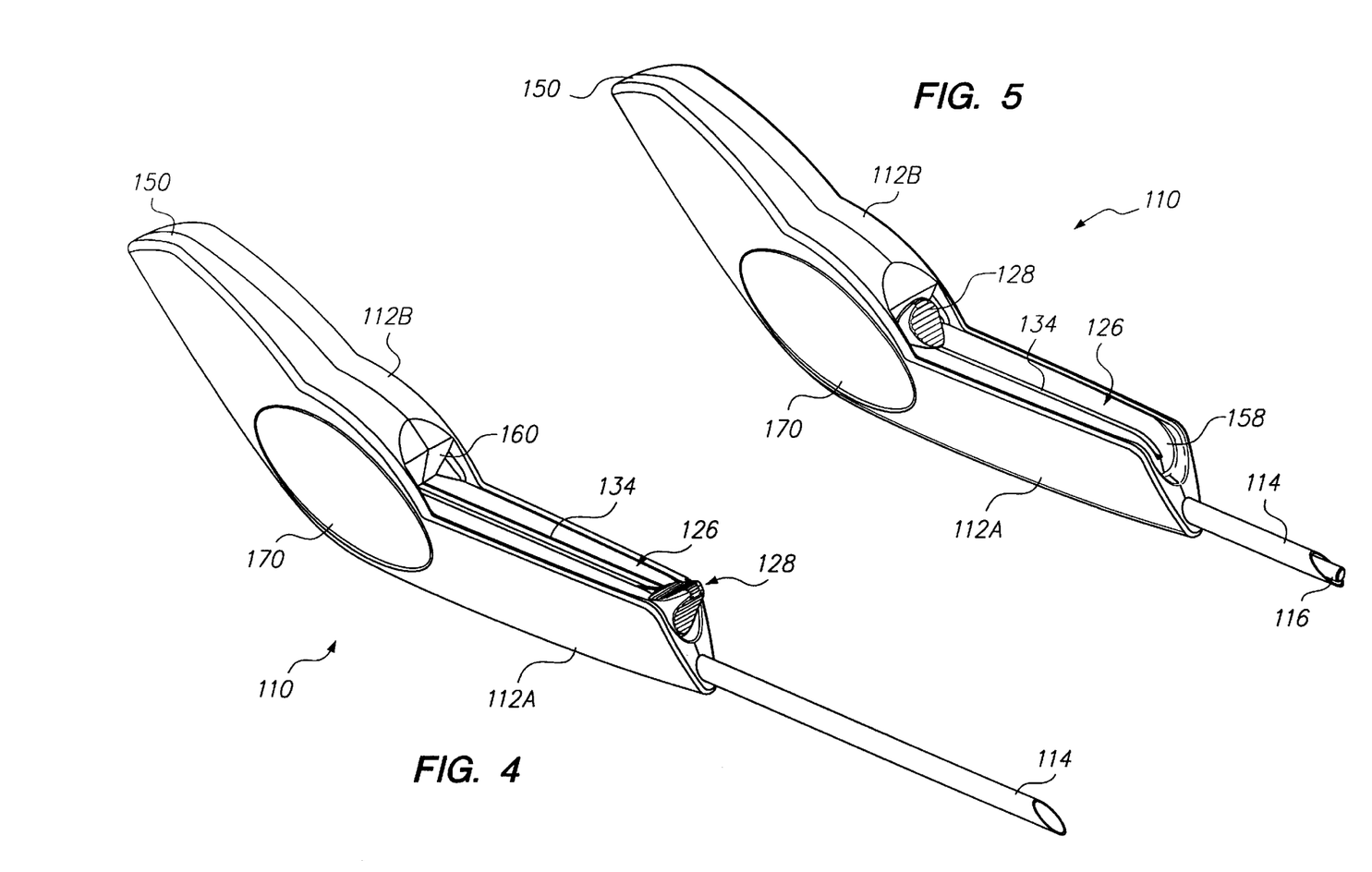
FIG. 4 is a perspective view of an implanter according to an alternative embodiment of the invention with the cannula in the extended position.
FIG. 5 is a perspective view of the implanter of FIG. 4 with the cannula in the retracted position.
Figure 6:
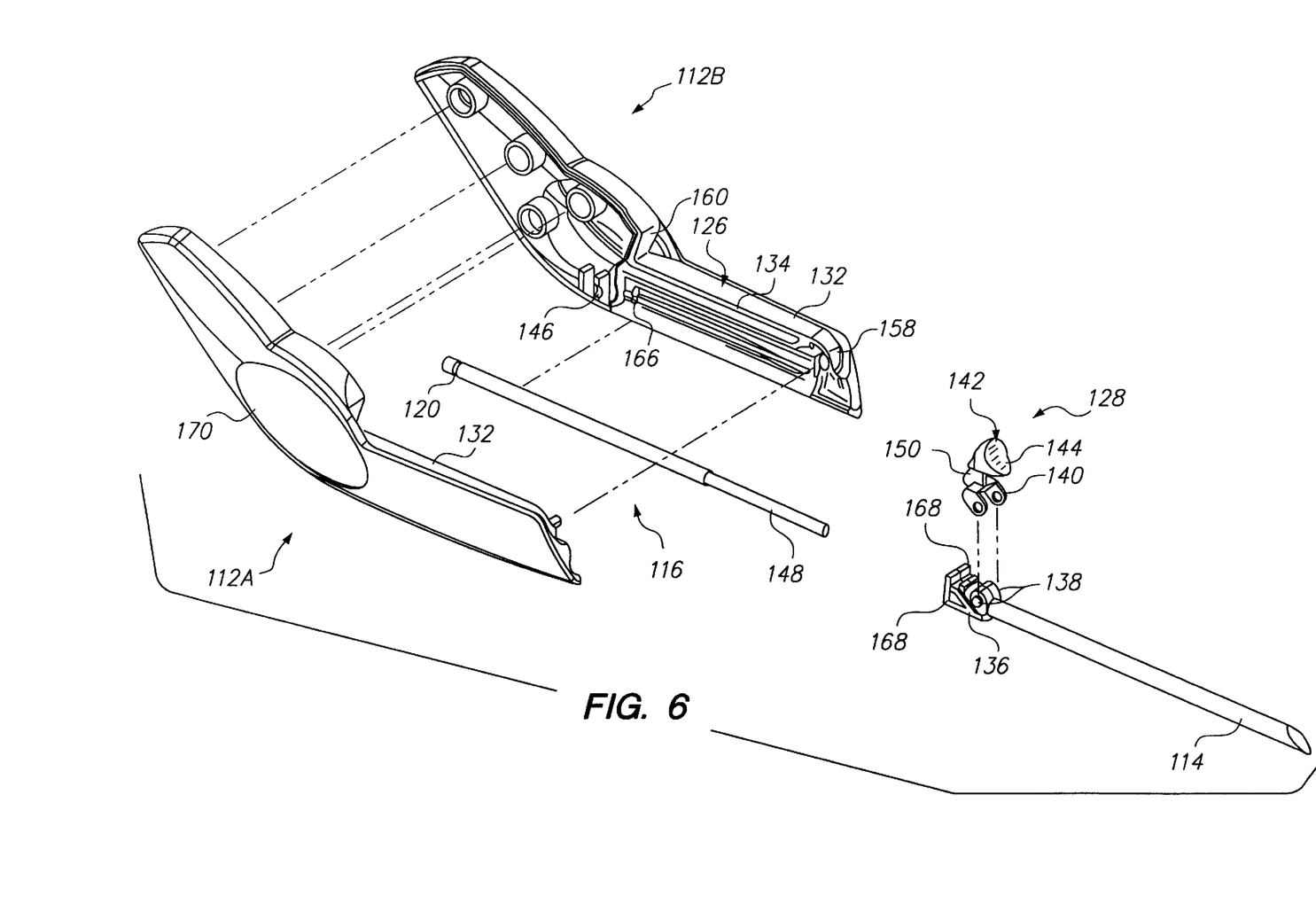
FIG. 6 is an exploded perspective view of the implanter of FIG. 4.

An alternative embodiment of the implanter according to the present invention is illustrated in FIGS. 4–6. The reference numerals used to describe the elements of the implanter 110 of FIGS. 4–6 correspond to reference numbers used to describe like elements in the embodiment of FIGS. 1–3 with a prefix of 1. The implanter 110 includes a handle having first and second halves 112A, 112B, a cannula 114 slidable in the handle, and a fixed rod 116. The cannula 114 is movable from the extended position of FIG. 4 to the retracted position of FIG. 5 by an actuator 128 to place an implant subcutaneously. The actuator 128 moves along a track 126 from a distal locking portion 158 of the track to a proximal recess 160.

The two handle portions 112A and 112B may be assembled in any known manner such as by ultrasonic welding, adhesive bonding, press-fit bosses, or a snap fit. The handle portions 112A, 112B each have an oval shaped indentation 170. The indentations 170 on opposite sides of the handle act as finger rests and indicate the locations at which the thumb and middle finger are placed to grasp the handle during operation of the implanter. A rear surface 150 of the handle rests against the palm of the user to steady the implanter 110 as the index finger moves the actuator 128 along the track 126. Pressure is also applied to the rear surface 150 by the palm of the user during insertion of the cannula 116.

The assembly of the implanter 110 will be described with reference to the exploded view of FIG. 6 which illustrates the implanter prior to assembly. As shown in FIG. 6, a proximal end of the rod 116 includes a circumferential groove 120 which is received between two fixing members 146, one of which is positioned within each half of the handle 112A, 112B. As the two handle halves 112A, 112B are assembled, the rod 116 is trapped between semi-circular cutouts of the fixing members 146 which receive in the rod groove 120. The rod 116 also includes a reduced diameter distal portion 148 which provides clearance for an implant retention feature of the cannula. The rod 116 includes a blunt distal end for engaging the implant.

The cannula 114 includes a cannula fitting 136 secured on the proximal end of the cannula for attachment of an actuator 128. The cannula fitting 136 is secured to the cannula by insert molding, press fitting, adhesive bonding, threading, ultrasonic staking, or the like. The actuator 128 is pivotally mounted on the cannula fitting 136 by engagement of a forked actuator base 140 with two pins 138 extending from opposite sides of the cannula fitting. The actuator 128 includes an enlarged portion or manipulator 142 having a ridged finger engaging surface 144. The forked actuator base 140 and the actuator manipulator 142 are connected by a connecting portion 150 which extends through a slot 134 of the track 126.

When the implanter 110 shown in FIGS. 4–6 is assembled, the actuator 128 is pivotally connected to the fitting 136 of the cannula 114. The actuator 128 slides within the track 126 from a distal portion of the track 158 which serves as a locking member to a recess 160 at a proximal end of the track. The angled distal portion 158 of the track 126 provides a locking feature which prevents unintended release of the implant by preventing withdrawal of the cannula 114 until the actuator 128 has been manually rotated out of the distal portion 158 of the track. The recess 160 at the proximal end of the track 126 receives the actuator 128 and discourages reuse of the implanter 110.

The implanter 110 also preferably includes a locking member 166 on an inside surface of at least one of the handle members 112A, 112B. The locking member 166 is a ramp shaped protrusion which engages a corresponding ramp shaped flange 168 on the cannula fitting 136. The locking member 166 and the flange 168 snap together when the cannula 114 is fully retracted to maintain the cannula locked in the retracted position. When the cannula 114 is fully retracted the user feels and hears the locking member 166 engage the flange 168 providing an audible and tactile indication of complete insertion. Alternatively, if reuse is desired the locking member 166 may be a smaller member which provides a tactile and/or audible indication of implant insertion without permanently locking the cannula in place.

The implanter 110 according to the present invention operates in a manner substantially similar to the manner of operation of the implanter 10 of FIG. 1. Preferably, the implanter 110 is a single-use device which is discarded after use, however, the implanter may also be reused if made of a sterilizable material.

The implanters 10, 110 according to both of the embodiments of the present invention described above preferably include one of the implant retaining features of FIGS. 7–10. The implant retaining mechanism holds the implant 18 in the cannula 14, 114 with a force which is easily overcome when the cannula is manually withdrawn over the implant and the rod 16, 116.

Figure 7:
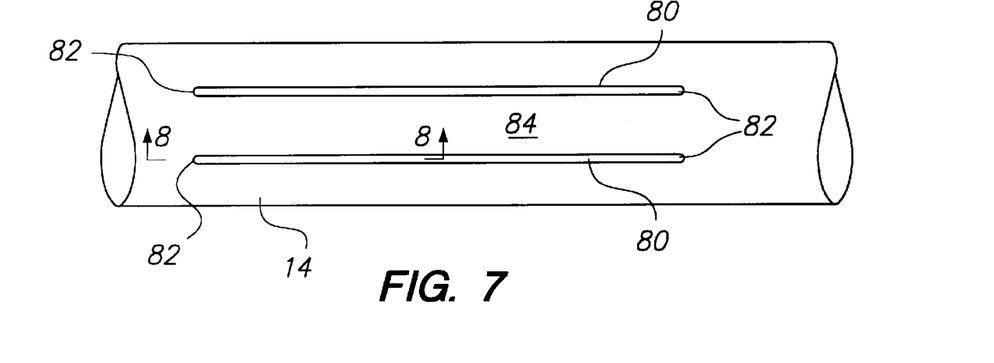
FIG. 7 is a bottom view of a portion of a cannula according to the present invention with a first embodiment of an implant retention mechanism.

As shown in FIG. 7, according to one preferred embodiment of the present invention, a cannula 14 includes two longitudinal slits 80 each having rounded ends 82. A portion 84 of the cannula 14 between the two slits 80 is permanently deformed inwardly by application of pressure perpendicular to the surface of the cannula substantially at a center of the portion 84 between the slits. The local deformation of the central portion 84 may be in the form of a bubble, a dome, a V-shape, or the like. The inwardly deformed portion 84 reduces the inner diameter of the cannula 14 at the location of the slits 80 and touches the implant with a force retaining the implant in the cannula. The force with which the implant is retained allows the implant to slide within the cannula 14 when the implant is inserted into the cannula and when the cannula is withdrawn by manipulation of the actuator 28. The retaining mechanism is preferably located on a bottom surface of the cannula 14 near a distal end of the cannula, however, the retaining mechanism may also be located at other positions on the cannula.

Figure 8:
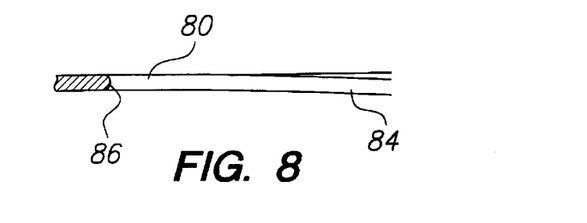
FIG. 8 is a partial cross sectional view of the cannula of FIG. 7 taken along line 8—8.

As shown in FIG. 8 which illustrates an enlarged cross-section of the slit 80, the edges 86 of the slit 80 are preferably rounded in cross-section to prevent tissue from being caught in the slits. Further, the ends 82 of the slits are rounded to substantially prevent crack propagation.

Figure 9:
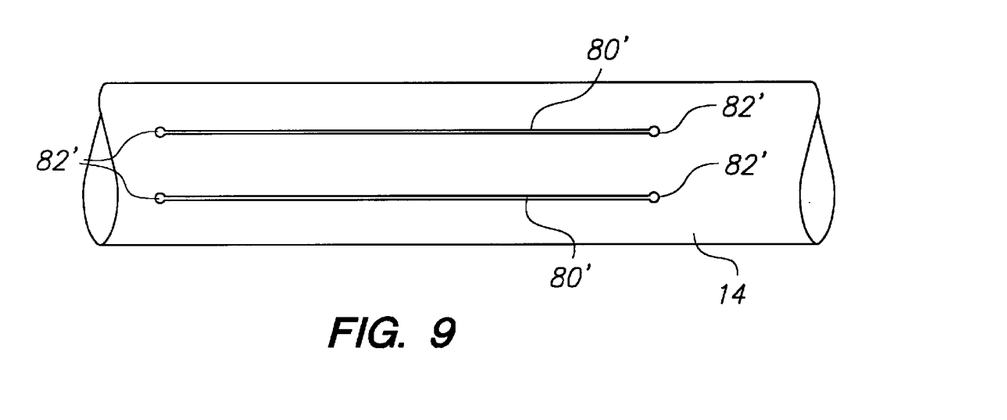
FIG. 9 is a bottom view of a portion of a cannula according to the present invention with a second embodiment of an implant retention mechanism.

The slit width is preferably as small as possible to prevent tissue from being caught in the slits. As shown in FIG. 9, the ends of narrow slits 80' are preferably enlarged circular ends 82'. The smaller slit width is less likely to snag tissue and the enlarged circular ends 82' prevent a stress riser and crack propagation at the ends of the smaller slits.

Figure 10:
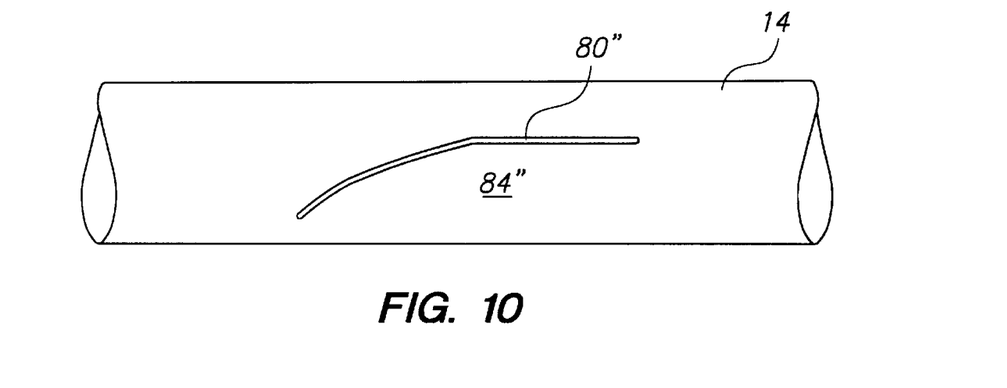
FIG. 10 is a bottom view of a portion of a cannula according to the present invention with a third embodiment of an implant retention mechanism.

According to an alternative embodiment illustrated in FIG. 10, a single curved or V-shaped slit 80" is used in place of the two parallel slits. A location 84" beside the single slit 80" is deformed inwardly by application of pressure perpendicular to the cannula 14. The deformed portion 84" provides a reduced inner diameter at the location of the slit 80" to retain the implant in the cannula 14. The reduced diameter portion provided by the retaining mechanisms is preferably as smooth as possible to prevent damage to the implant.

The cannula 14 has been described as a metal cannula having a deformed implant retaining portion which is locally deformed to project into an inner diameter of the cannula and retain the implant. However, the implant retaining portion can be formed in other manners such as by addition of an implant retaining member to an inner diameter of the cannula or by molding an element within the cannula.

Figures 11, 11A, 12:
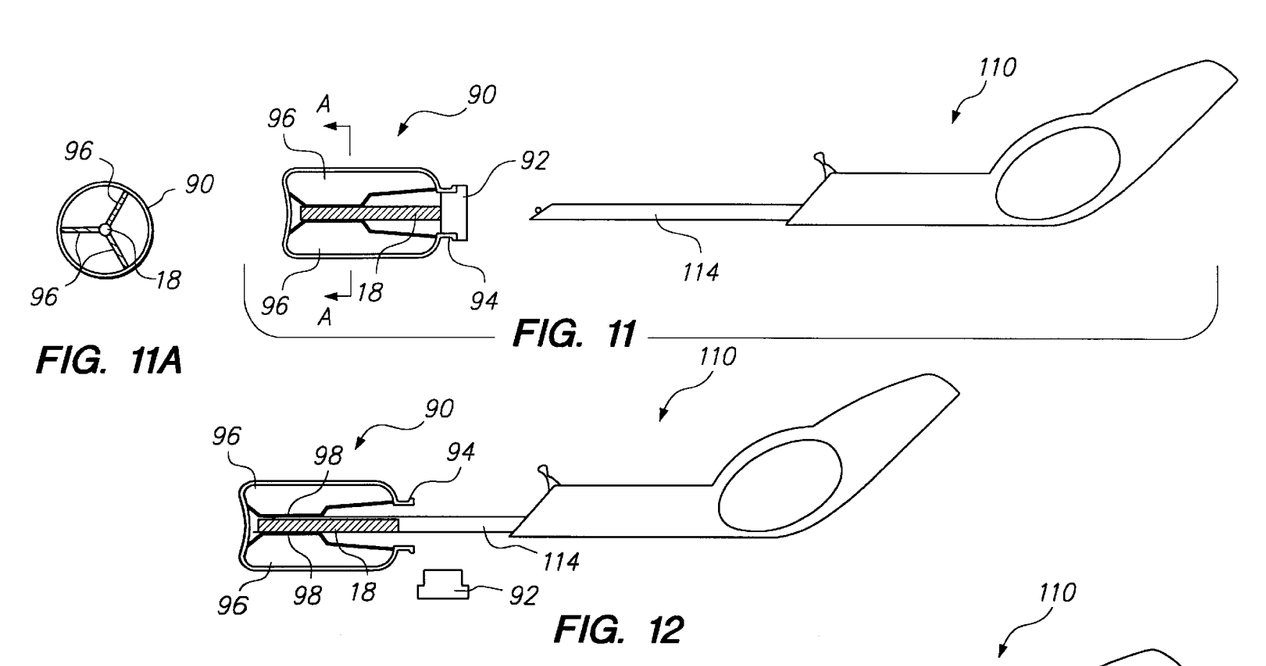
FIG. 11 is a schematic side view of an implanter and an implant vial according to the present invention.
FIG. 11A is a cross-sectional view taken along line A—A of FIG. 11.
FIG. 12 is a schematic side view of the implanter receiving an implant from the vial.
Figure 13:
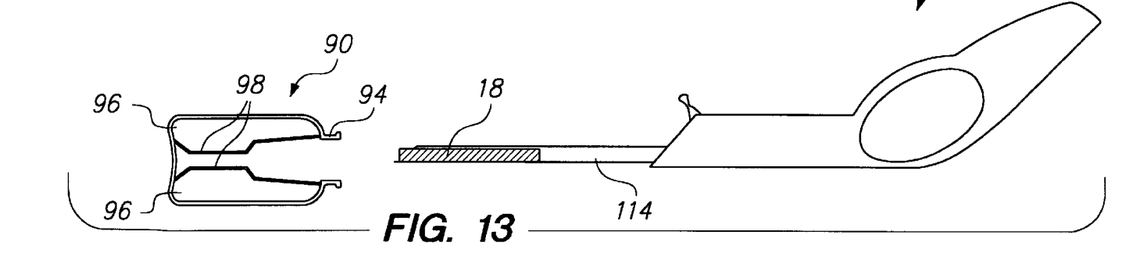
FIG. 13 is a schematic side view of an implanter loaded with an implant.

FIGS. 11–13 illustrate one preferred method for loading the implant 18 into the implanter 110 in the case where the implanter is not preloaded by employing an implant containing vial 90. The vial 90 maintains the implant in a sterile condition during transportation, storage, and loading. The implant 18 is positioned within the vial 90 in a centered position by one or more centering members and a stopper 92 is placed in a neck 94 of the vial. As shown in FIG. 11A, which is a cross sectional view of the vial 90, the implant 18 is centered in the vial by three radial implant supports 96. The radial implant supports 96 include exterior surfaces which are configured to engage the side walls of the vial 90 and parallel interior surfaces 98 for engaging and supporting the implant 18.

In operation, the implant 18 is loaded into the implanter device 110 as shown in FIGS. 11–13 by removing the stopper 92 from the vial 90, and sliding the cannula 114 of the implanter over the implant which is centered in the vial. Once the implant 18 is fully contained within the cannula 114, the implanter 110 is withdrawn from the vial 90 and the implant is held in place in the implanter cannula by one of the retention features described above until time for implantation. The neck 94 of the vial may include a conical shaped member (not shown) which acts as a guiding member to guide the cannula 114 onto the implant 18. In addition, the implant 18 may be secured in the center of the vial 90 in other manners such as by a cylindrical flange on a bottom surface of the vial, as long as the implant is positioned with its longitudinal axis aligned with the neck 94 for the vial so that the implant can be received in the cannula 114 of the implanter 110.

The vial 90 allows the implant 18 to be maintained in a sterile condition until it is removed from the vial directly by the implanter 110. The removal of the implant 18 from the vial directly into the implanter 110 avoids possible contamination which may occur when an implant is removed from a vial manually and inserted into the implanter. Although the implant loading system has been illustrated with the implanter 110 of FIGS. 4–6 it should be understood that the loading system is intended to be used with any of the embodiments of the present invention.

Figure 14:
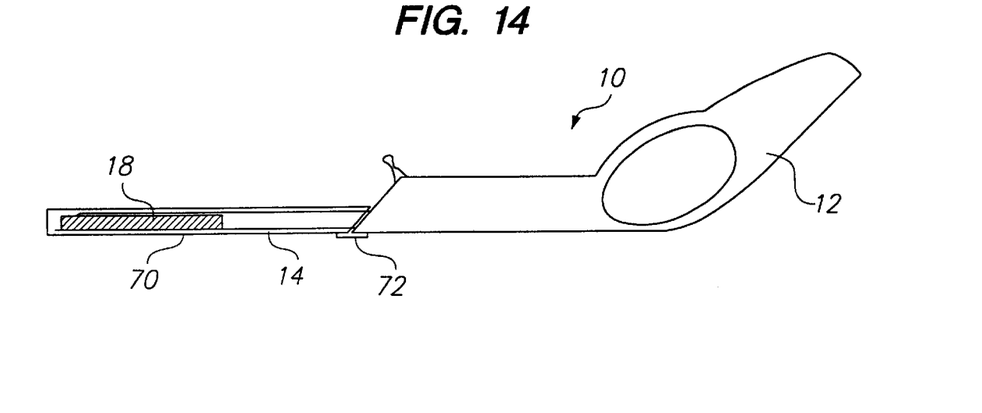
FIG. 14 is a schematic side view of an implanter with a safety sleeve for loading the implant.

According to an alternative embodiment, the implant 18 may be loaded into the implanter 10 by hand or by the use of forceps. When loading the implanter by hand a hollow sleeve 70, as shown in FIG. 14, may be placed over the cannula 14 extending just past the angled distal tip of the cannula. The hollow sleeve 70 prevents pricking of the hand or glove while inserting the implant into the cannula. The sleeve 70 may be removably secured to the cannula 14 or to the handle 12 by an adhesive strip 72 or by other securing means.

Figure 15:
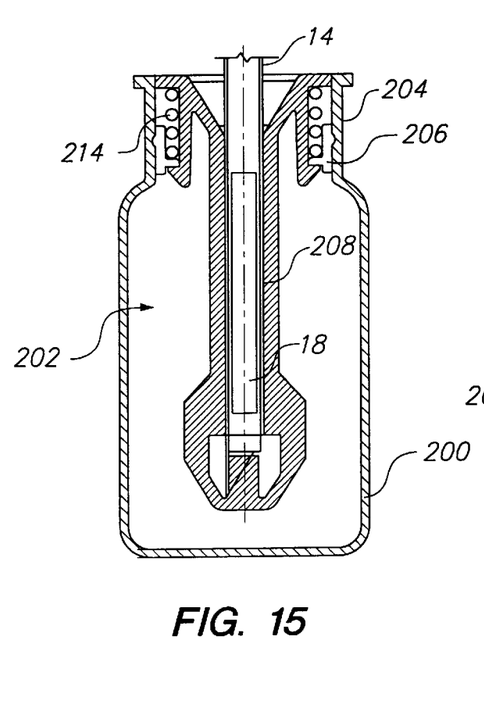
FIG. 15 is a side cross sectional view of an alternative embodiment of the vial.
Figure 16:
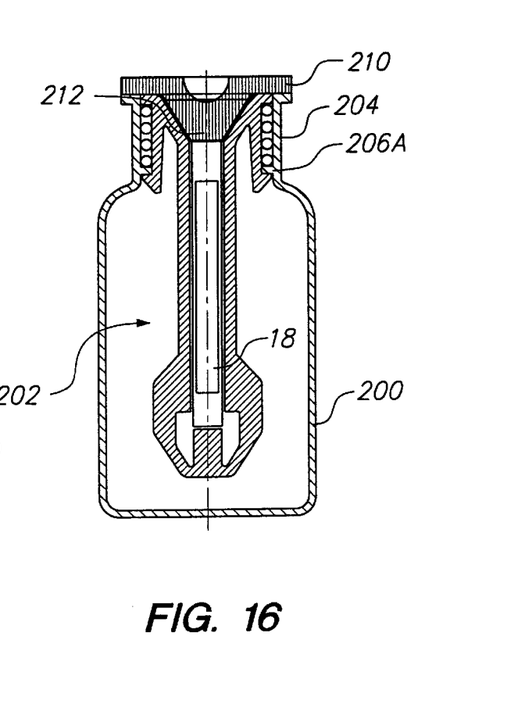
FIG. 16 is a side cross sectional view of another alternative embodiment of the vial.
Figure 17:
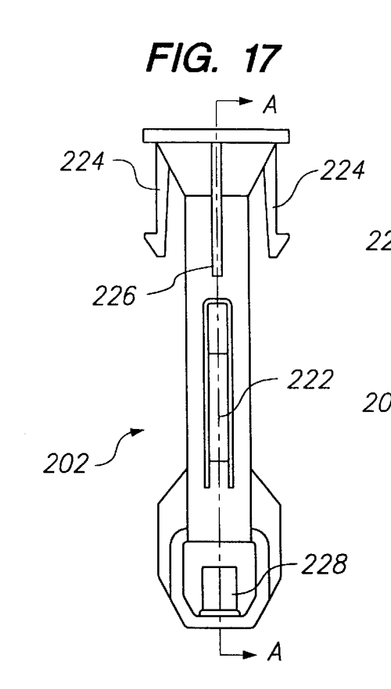
FIG. 17 is a front view of the implant holding member for the vials of FIGS. 15 and 16.
Figure 18:
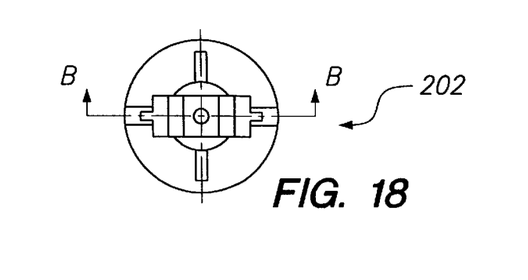
FIG. 18 is a bottom view of the implant holding member of FIG. 17.
Figure 19:
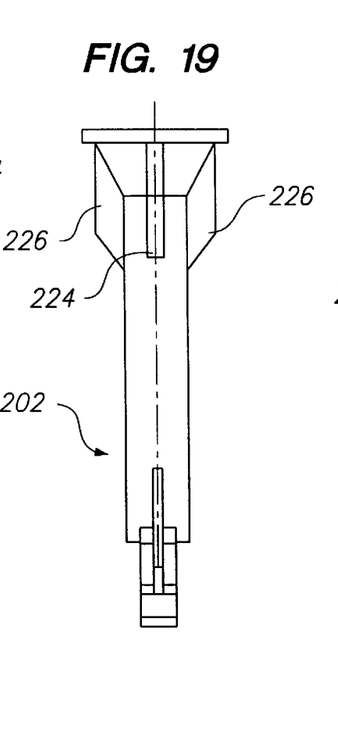
FIG. 19 is side view of the implant holding member of FIG. 17.

FIGS. 15–21 illustrate another preferred embodiment of a vial 200 having an implant holding member 202 holding the implant 18 in a centered position within the vial for loading into the cannula 14 of the implanter. The vial 200 includes a neck 204 having a locking step insert ring 206 secured within the neck for locking the implant holding insert 202 in place in the vial. Alternatively, the locking step 206a may be formed in the vial as shown in FIG. 16. The insert 202 has a central opening 208 in which the implant 18 is received with a certain amount of play which will allow the cannula 14 of the implanter 10 to be inserted into the vial around the implant to remove the implant from the vial.

As shown in FIG. 16, a stopper 210 is placed on the vial 200 and secured in place by a threaded or crimped on cap (not shown), preferably having a tear off portion for access to the stopper. The stopper 210 has a sealing surface 212 which extends down to and engages an end of the implant 18 to provide a seal for the dispensing opening in the end of the implant. The location of the sealing surface 212 of the stopper will vary depending on the size, particularly the length, of the implant 18.

A spring 214 is provided in the vial neck 204 which preferably applies as constant a force as possible between the implant holding insert 202 and the insert ring 206 to keep the stopper 210 in sealing contact with the dispensing opening in the implant and prevent leakage of the beneficial agent from the implant. The sterility of the implant 18 is maintained by a hermetic seal formed by the vial stopper 210 seating against the insert 202 and vial 200. The spring 214 accommodates dimensional changes in the stopper 210 and the insert 202 which may cause a loss of sealing.

Figure 20:
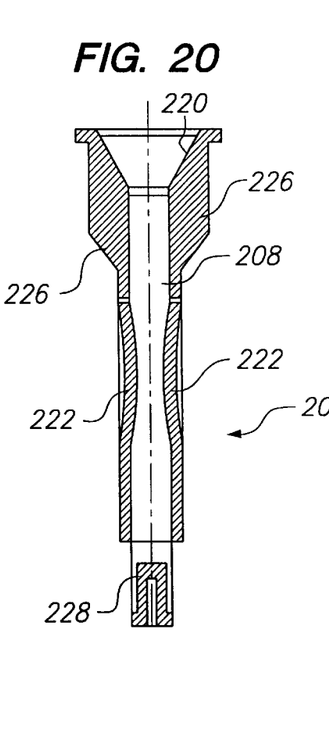
FIG. 20 is a side cross sectional view of the implant holding member taken along line A—A of FIG. 17.
Figure 21:
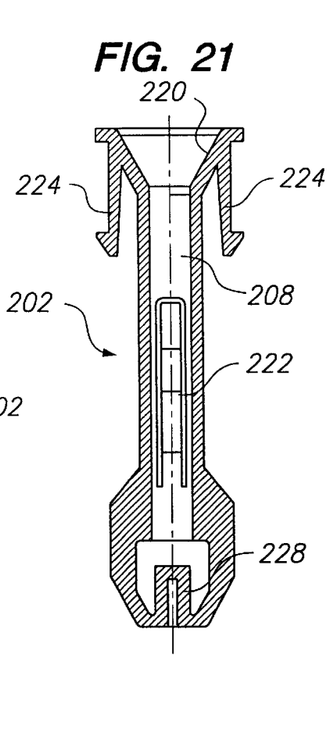
FIG. 21 is a front cross sectional view of the implant holding member taken along line B—B of FIG. 18.

The implant holding insert 202 is illustrated in FIGS. 17–21 and includes a tapered mouth 220 for guiding the cannula 14 into the vial 200. The central opening 208 for receiving and retaining the implant 18 extends from the tapered mouth 220. Adjacent the central opening 208 are two spring loaded arms 222 which curve inward as shown in FIG. 20 and retain the implant in the vial. The insert 202 is held in place and centered in the vial 200 by two locking arms 224 and two centering arms 226. However, other numbers of locking arms 224 and centering arms 226 may also be used. The centering arms 226 center the insert 202 within the insert ring 206, 206a and the locking arms 224 lock the insert 202 into the vial by snapping over the insert ring while allowing the insert 202 to move within the vial during insertion of the cannula 14 into the vial to remove the implant 18.

The bottom of the central opening 208 is provided with a stand off 228 which has a diameter somewhat smaller than an inner diameter of the cannula 14. The stand off 228 allows the beveled end of the cannula 14 to extend around the stand off, as shown in FIG. 15 so that the implant 18 can be inserted into the cannula either entirely or with a small corner of the implant exposed.

In operation, the stopper 210 is removed from the vial 200 and the cannula 14 of the implanter 10 is simply inserted into the vial to remove the implant from the vial. When the cannula 14 is fully inserted into the vial 200, the implant 18 is positioned properly in place within the cannula. The cannula 14 is then removed from the vial 200 and is ready for use in insertion of the implant 18. The vial 200 maintains the sterility of the implant during storage, transport, and loading of the implant 18 into the implanter 10.

Figure 22:
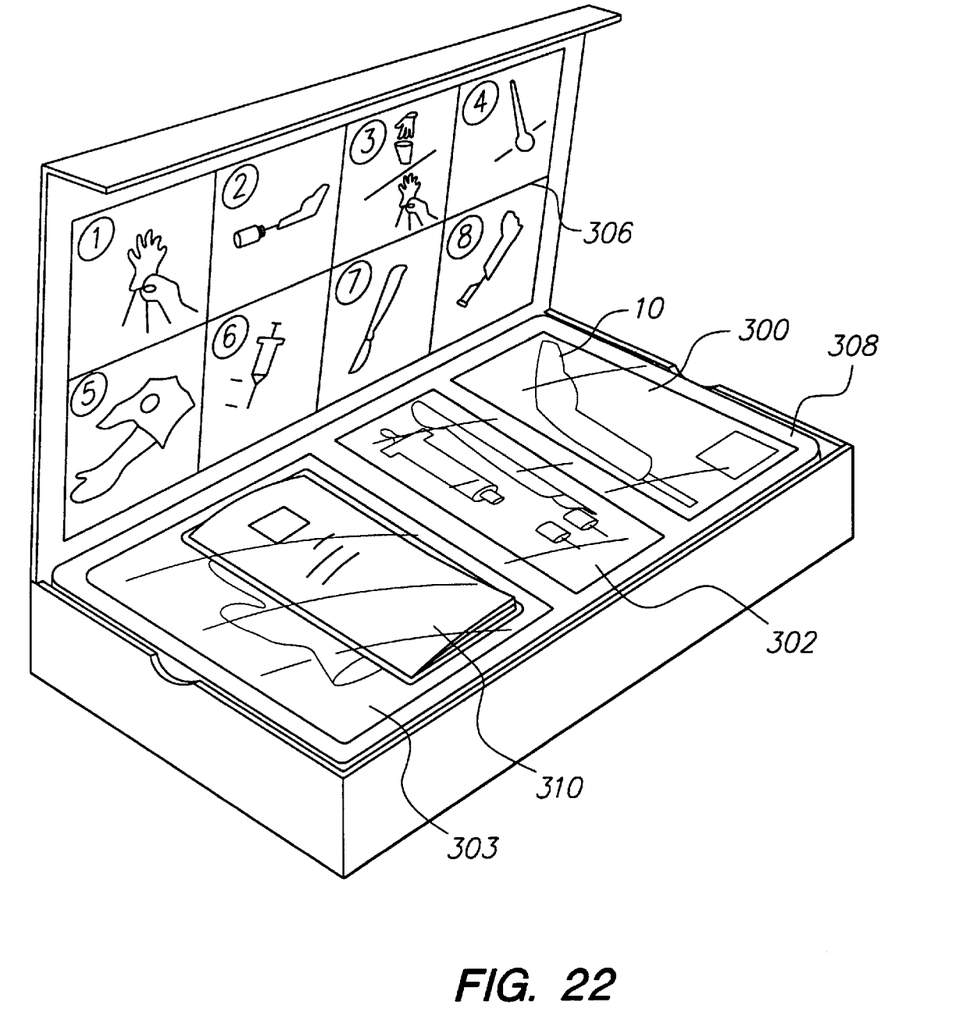
FIG. 22 is a perspective view of a kit according to the present invention.

FIG. 22 shows a kit for inserting an implant and maintaining sterile conditions during implant insertion. The kit includes the implanter 10 in a first compartment 300. A second compartment 302 includes a syringe, needles, scalpel, and any other instruments needed. A third compartment 304 includes gloves, drapes, wound dressings and other procedural supplies for maintaining sterility of the implanting process, as well as an instruction booklet 310. A cover 306 of the kit may include illustrations of the implanting procedure and a clear plastic cover 308 may be placed over the compartments to maintain sterility.

While the invention has been described in detail with reference to a preferred embodiment thereof, it will be apparent to one skilled in the art that various changes and modifications can be made, and equivalents employed, without departing from the spirit and scope of the invention.

What is claimed is:

1. An implanter for inserting implants comprising:
   a handle for grasping the implanter during insertion of an implant, the handle having a distal end, a proximal end, and a track formed along a first surface of the handle;
   a rod longitudinally fixed to the handle, the rod extending from the distal end of the handle;

a hollow cannula positioned coaxially around and longitudinally slidable over the rod from an extended position in which an implant is retained in the cannula to a retracted position in which the implant is released from the cannula; and an actuator connected pivotally to the cannula and slidable in the track of the handle to move the cannula from the extended position to the retracted position to release the implant from the cannula, wherein the actuator pivots between a locked and an unlocked position.

2. The implanter for inserting implants according to claim 1, wherein a distal end of the track includes a locking portion and the actuator engages the locking portion to prevent retraction of the cannula.

3. The implanter for inserting implants according to claim 2, wherein the locking portion of the track is formed at a distal end of the track and is angled with respect to a remainder of the track.

4. The implanter for inserting implants according to claim 1, wherein the actuator includes an interior portion located inside the handle, a manipulating portion located outside the handle, and a connecting portion connecting the interior and exterior portions.

5. The implanter for inserting implants according to claim 4, wherein the track includes a slot in the handle through which the connecting portion of the actuator extends.

6. The implanter for inserting implants according to claim 4, wherein a proximal end of the track includes a recess configured to receive the manipulating portion within the handle when the cannula is in the retracted position.

7. The implanter for inserting implants according to claim 1, in combination with an osmotic subcutaneous implant configured to be received inside a distal end of the cannula.

8. The implanter for inserting implants according to claim 1, wherein the cannula has a beveled distal end which does not cut unbroken skin.

9. The implanter for inserting implants according to claim 1, wherein the actuator is locked to the handle in a retracted position to prevent reuse.

10. The implanter for inserting implants according to claim 1, wherein the cannula includes at least one slot providing a retention mechanism for retaining the implant in the cannula.

11. An implanter for inserting implants comprising:

a handle for grasping the implanter during insertion of an implant, the handle having a distal end, a proximal end, and a track formed along a first surface of the handle, wherein a distal end of the track includes a locking portion which is angled with respect to a remainder of the track;

a rod longitudinally fixed to the handle, the rod extending from the distal end of the handle;

a hollow cannula positioned coaxially around and longitudinally slidable over the rod from an extended position in which an implant is retained in the cannula to a retracted position in which the implant is released from the cannula; and an actuator connected to the cannula and slidable in the track of the handle to move the cannula from the extended position to the retracted position to release the implant from the cannula, wherein the actuator engages the locking portion to prevent retraction of the cannula.

12. A method of inserting an implant subcutaneously with an implanter comprising:

inserting a cannula of an implanter beneath the skin of a patient with an implant positioned within the cannula, the implanter including a handle and a slidable actuator pivotally attached to the cannula;

unlocking the activator by pivoting then actuator with respect to the cannula from a locked to an unlocked position;

manually retracting the cannula by sliding the actuator along a track in the handle to release the implant beneath the skin; and withdrawing the implant from the patient.

\* \* \* \* \*

UNITED STATES PATENT AND TRADEMARK OFFICE
CERTIFICATE OF CORRECTION

| | | |
|---|---|---|
| PATENT NO. | : 6,190,350 B1 | Page 1 of 1 |
| APPLICATION NO. | : 09/217824 | |
| DATED | : February 20, 2001 | |
| INVENTOR(S) | : Craig R. Davis et al. | |

It is certified that error appears in the above-identified patent and that said Letters Patent is hereby corrected as shown below:

Column 12, line 31, in claim 12 delete "activator" and replace with --actuator-- and delete "then" and replace with --the--.

Column 12, line 37, in claim 12 delete "implant" and replace with --implanter--.

Signed and Sealed this

Twenty-third Day of June, 2009

JOHN DOLL
*Acting Director of the United States Patent and Trademark Office*

UNITED STATES PATENT AND TRADEMARK OFFICE
CERTIFICATE OF CORRECTION

| | | |
|---|---|---|
| PATENT NO. | : 6,190,350 B1 | Page 1 of 1 |
| APPLICATION NO. | : 09/217824 | |
| DATED | : February 20, 2001 | |
| INVENTOR(S) | : Craig R. Davis et al. | |

It is certified that error appears in the above-identified patent and that said Letters Patent is hereby corrected as shown below:

Title page, item (75) inventors: Delete "both of CA", insert --Scott Gilbert, Menlo Park, All of CA--.

Signed and Sealed this

Fifteenth Day of September, 2009

David J. Kappos
*Director of the United States Patent and Trademark Office*